(12) United States Patent
Hourmand et al.

(10) Patent No.: US 9,707,356 B2
(45) Date of Patent: *Jul. 18, 2017

(54) AUTO-INJECTOR

(75) Inventors: Yannick Hourmand, Haslingfield (GB); Timothy Donald Barrow-Williams, St. Albans (GB); Matthew Ekman, Macclesfield (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 34 days.

This patent is subject to a terminal disclaimer.

(21) Appl. No.: 13/807,268

(22) PCT Filed: Jun. 20, 2011

(86) PCT No.: PCT/EP2011/060504
§ 371 (c)(1),
(2), (4) Date: Aug. 13, 2013

(87) PCT Pub. No.: WO2012/000872
PCT Pub. Date: Jan. 5, 2012

(65) Prior Publication Data
US 2013/0310759 A1  Nov. 21, 2013

Related U.S. Application Data

(60) Provisional application No. 61/413,799, filed on Nov. 15, 2010.

(30) Foreign Application Priority Data

Jun. 28, 2010 (EP) .................................. 10167480

(51) Int. Cl.
*A61M 5/32* (2006.01)
*A61M 5/20* (2006.01)
(Continued)

(52) U.S. Cl.
CPC ........ *A61M 5/3221* (2013.01); *A61M 5/2033* (2013.01); *A61M 5/31511* (2013.01);
(Continued)

(58) Field of Classification Search
CPC .. A61M 5/3243; A61M 5/3219; A61M 5/322; A61M 5/3221; A61M 5/3202;
(Continued)

(56) References Cited

U.S. PATENT DOCUMENTS 5,042,977 A * 8/1991 Bechtold ................. A61M 5/20
604/134
5,267,963 A  12/1993 Bachynsky
(Continued)

FOREIGN PATENT DOCUMENTS

GB WO 2009081103 A1 * 7/2009 .......... A61M 5/2033
WO 2009062508 A1 5/2009
WO 2009081103 A1 7/2009

*Primary Examiner* — Bhisma Mehta
*Assistant Examiner* — Larry R Wilson
(74) *Attorney, Agent, or Firm* — Fish & Richardson P.C.

(57) ABSTRACT

An auto-injector comprising a housing containing a syringe with a hollow needle and a stopper for sealing the syringe and displacing the medicament. A spring capable of, upon activation: pushing the needle from a covered position inside the housing into an advanced position through the orifice and past the proximal end, operating the syringe to supply the dose of medicament, and retracting the syringe with the needle into the covered position after delivering the medicament. A trigger locks the spring in a pressurized state prior to operation and, upon manual operation, releasing the spring for injection. An interlock sleeve telescoped in the housing and translatable in longitudinal direction, wherein in a proximal position the interlock sleeve is arranged to be coupled to the syringe in the syringe's retracted position and (Continued)

wherein the interlock sleeve in its distal position is arranged to allow decoupling of the syringe.

16 Claims, 6 Drawing Sheets

(51) Int. Cl.
    *A61M 5/315*     (2006.01)
    *A61M 5/46*     (2006.01)

(52) U.S. Cl.
    CPC ............... *A61M 5/326* (2013.01); *A61M 5/46* (2013.01); *A61M 2005/206* (2013.01); *A61M 2005/208* (2013.01)

(58) Field of Classification Search
    CPC .......... A61M 5/31535; A61M 5/31583; A61M 5/1454; A61M 2005/31508; A61M 5/20; A61M 5/2033; A61M 5/3257; A61M 5/326; A61M 2005/206; A61M 2005/208
    USPC ................. 604/135–137, 187, 192, 196–198
    See application file for complete search history.

(56) References Cited

U.S. PATENT DOCUMENTS

| | | | |
|---|---|---|---|
| 7,361,160 B2 * | 4/2008 | Hommann et al. | 604/198 |
| 7,445,613 B2 * | 11/2008 | Hommann | 604/211 |
| 7,717,877 B2 | 5/2010 | Lavi et al. | |
| 8,956,331 B2 * | 2/2015 | Johansen | A61M 5/2033 604/135 |
| 2002/0095120 A1 * | 7/2002 | Larsen et al. | 604/187 |
| 2005/0261634 A1 * | 11/2005 | Karlsson | 604/197 |
| 2009/0275916 A1 * | 11/2009 | Harms et al. | 604/506 |

\* cited by examiner

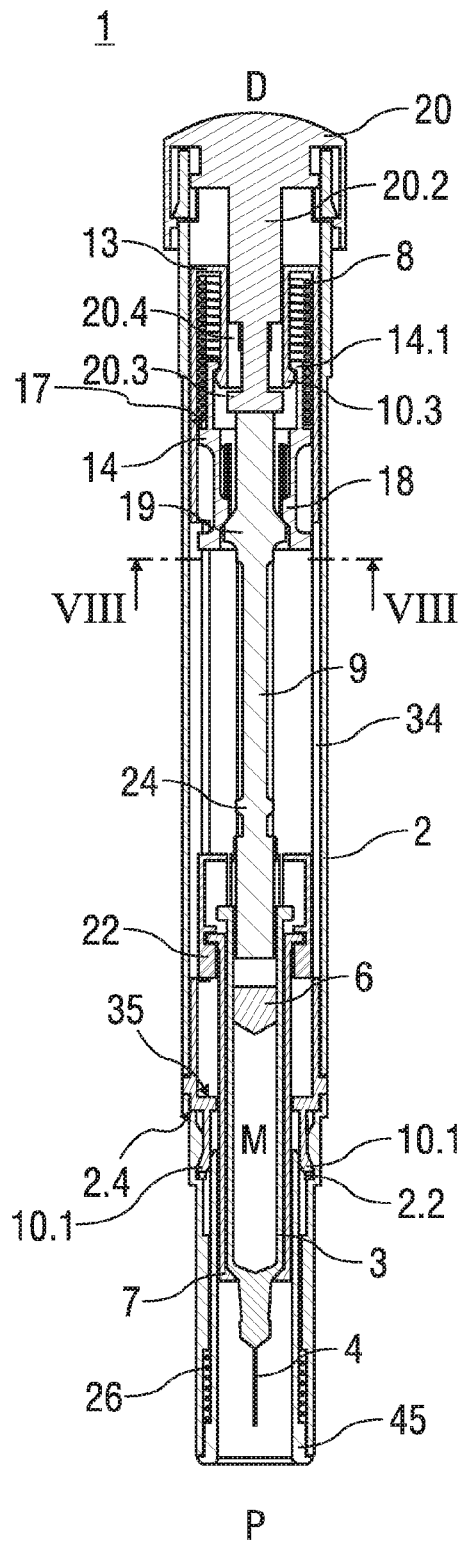
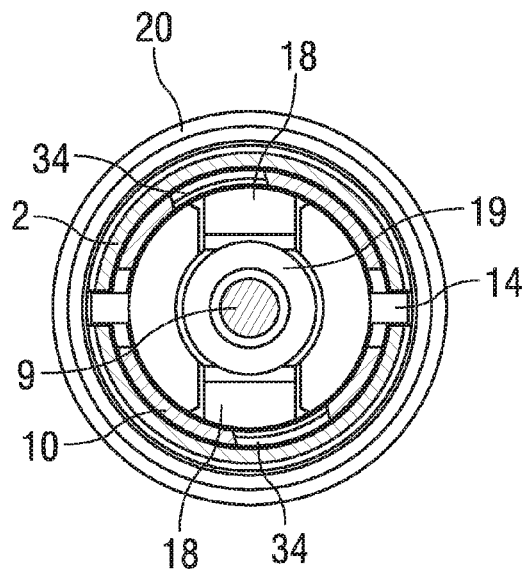
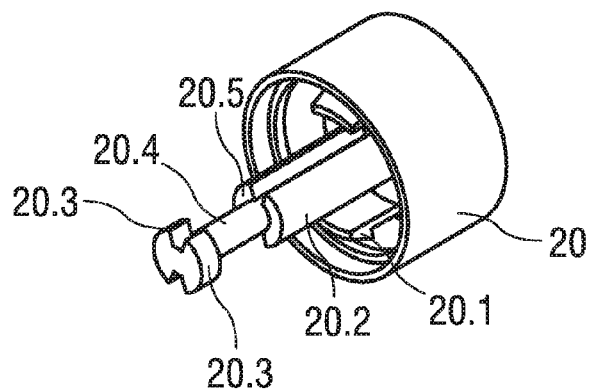

AUTO-INJECTOR

CROSS REFERENCE TO RELATED APPLICATIONS

The present application is a U.S. National Phase Application pursuant to 35 U.S.C. §371 of International Application No. PCT/EP2011/060504 filed Jun. 22, 2011, which claims priority to European Patent Application No. 10167480.2 filed Jun. 28, 2010 and U.S. Patent Application No. 61/413,799 filed Nov. 15, 2010. The entire disclosure contents of these applications are herewith incorporated by reference into the present application.

FIELD OF INVENTION

The invention relates to an auto-injector for administering a dose of a liquid medicament according to the preamble of claim 1.

BACKGROUND

Administering an injection is a process which presents a number of risks and challenges for users and healthcare professionals, both mental and physical.

Injection devices (i.e. devices capable of delivering medicaments from a medication container) typically fall into two categories—manual devices and auto-injectors.

In a manual device—the user must provide the mechanical energy to drive the fluid through the needle. This is typically done by some form of button/plunger that has to be continuously pressed by the user during the injection. There are numerous disadvantages to the user from this approach. If the user stops pressing the button/plunger then the injection will also stop. This means that the user can deliver an underdose if the device is not used properly (i.e. the plunger is not fully pressed to its end position). Injection forces may be too high for the user, in particular if the patient is elderly or has dexterity problems.

The extension of the button/plunger may be too great. Thus it can be inconvenient for the user to reach a fully extended button. The combination of injection force and button extension can cause trembling/shaking of the hand which in turn increases discomfort as the inserted needle moves.

Auto-injector devices aim to make self-administration of injected therapies easier for patients. Current therapies delivered by means of self-administered injections include drugs for diabetes (both insulin and newer GLP-1 class drugs), migraine, hormone therapies, anticoagulants etc.

Auto-injectors are devices which completely or partially replace activities involved in parenteral drug delivery from standard syringes. These activities may include removal of a protective syringe cap, insertion of a needle into a patient's skin, injection of the medicament, removal of the needle, shielding of the needle and preventing reuse of the device. This overcomes many of the disadvantages of manual devices. Injection forces/button extension, hand-shaking and the likelihood of delivering an incomplete dose are reduced. Triggering may be performed by numerous means, for example a trigger button or the action of the needle reaching its injection depth. In some devices the energy to deliver the fluid is provided by a spring.

US 2002/0095120 A1 discloses an automatic injection device which automatically injects a pre-measured quantity of fluid medicine when a tension spring is released. The tension spring moves an ampoule and the injection needle from a storage position to a deployed position when it is released. The content of the ampoule is thereafter expelled by the tension spring forcing a piston forward inside the ampoule. After the fluid medicine has been injected, torsion stored in the tension spring is released and the injection needle is automatically retracted back to its original storage position.

The spring means is a single compression spring arranged to be grounded at a distal end in the housing for advancing the needle and for injecting the dose of medicament via a plunger and wherein the compression spring is arranged to have its ground in the housing switched to its proximal end for retracting the syringe.

SUMMARY

It is an object of the present invention to provide an improved auto-injector with a means for reducing the risk of inadvertent triggering.

The object is achieved by an auto-injector according to claim 1.

Preferred embodiments of the invention are given in the dependent claims.

In the context of this specification the term proximal refers to the direction pointing towards the patient during an injection while the term distal refers to the opposite direction pointing away from the patient.

According to the invention, an auto-injector for administering a dose of a liquid medicament comprises:

an elongate housing arranged to contain a syringe with a hollow needle and a stopper for sealing the syringe and displacing the medicament, the housing having a distal end and a proximal end with an orifice intended to be applied against an injection site, wherein the syringe is slidably arranged with respect to the housing, spring means capable of, upon activation:

pushing the needle from a covered position inside the housing into an advanced position through the orifice and past the proximal end, operating the syringe to supply the dose of medicament, and retracting the syringe with the needle into the covered position after delivering the medicament, activating means arranged to lock the spring means in a pressurized state prior to manual operation and capable of, upon manual operation, releasing the spring means for injection.

According to the invention the spring means is a single drive spring in the shape of a compression spring arranged to be grounded at a distal end in the housing for advancing the needle and for injecting the dose of medicament. The force of the drive spring is forwarded to the needle and/or the syringe via a plunger. The drive spring is arranged to have its ground in the housing switched to its proximal end for retracting the syringe when the injection of the medicament is at least nearly finished.

The single drive spring is used for inserting the needle, fully emptying the syringe and retracting the syringe and needle to a safe position after injection. Thus a second spring for withdrawing the syringe and needle, which is a motion with an opposite sense compared to advancing the syringe and injecting the dose, is not required. While the distal end of the drive spring is grounded the proximal end moves the syringe forward for inserting the needle and carries on to the injection by pushing on the stopper. When the injection is at least nearly finished the drive spring bottoms out at its proximal end, resulting in the proximal end being grounded in the housing. At the same time the distal end of the drive spring is released from its ground in the housing. The drive spring is now pulling the syringe in the opposite direction.

According to the invention an interlock sleeve is telescoped in the proximal end of the housing, the interlock sleeve translatable in longitudinal direction between a proximal position and a distal position and biased in proximal direction in a manner to protrude from the housing in the proximal position, wherein in its proximal position the interlock sleeve is arranged to be coupled to the syringe in the syringe's retracted position for joint axial movement and wherein the interlock sleeve in its distal position is arranged to allow decoupling of the syringe.

In an as delivered state of the auto-injector the interlock sleeve is in its proximal position protruding from the proximal end of the housing. The syringe and needle are in their retracted position. As the interlock sleeve and the syringe are coupled for joint axial movement the syringe and needle cannot advance even if the spring means were inadvertently released by operating the activating means. Thus the needle remains in its covered position. In order to trigger an injection the auto-injector has to be pressed with its proximal end against an injection site, e.g. a patient's skin in a manner to translate the interlock sleeve in distal direction into the housing. Thus the syringe is decoupled or allowed to decouple from the interlock sleeve and may now translate so as to move the needle into its advanced position for piercing the patient's skin. Before the syringe and needle actually translate in proximal direction the activating means has to be operated so as to release the drive spring. The probability for inadvertent operation of the auto-injector thus decreases due to the requirement of two user actions, pressing the auto-injector against the injection site and operating the activating means.

The auto-injector according to the invention has a particularly low part count compared to most conventional auto-injectors. The use of just one drive spring reduces the amount of metal needed and thus consequently reduces weight and manufacturing costs.

It is desirable to trigger the refraction of the needle when the contents of the syringe have been entirely delivered to the patient, i.e. when the stopper has bottomed out in the syringe. Automatically triggering the retraction when the stopper exactly reaches the end of its travel is a problem due to tolerances when manufacturing the syringe and stopper. Due to these tolerances the position of the stopper relative to the means triggering retraction at the end of its travel is not repeatable. Consequently, in some cases the stopper would prematurely bottom out so the retraction would not be triggered at all. In other cases the retraction would be triggered before the stopper bottomed so residual medicament would remain in the syringe.

The retraction could automatically be triggered a certain amount of time or travel before the stopper bottoms out in the syringe. However this reliable retraction would be traded off for residual medicament in the syringe.

Thus, in a preferred embodiment the interlock sleeve is furthermore arranged to prevent release of the distal ground of the drive spring when in the distal position. This means, the drive spring remains distally grounded as long as the auto-injector is kept pressed against the injection site so the needle retraction can only start when the auto-injector is removed from the injection site and the interlock sleeve consequently returns into its proximal position and thus releases the distal ground. Full delivery of the medicament and reliable retraction are thus achieved by waiting for the user action of removing the auto-injector from the injection site.

A retraction sleeve may be axially movable arranged in the housing, wherein the drive spring is arranged inside the retraction sleeve with its distal end bearing against a distal end face and with its proximal end bearing against a thrust face of a decoupling member. At least one resilient wedge may be arranged at the proximal end of the refraction sleeve, wherein the housing has a respective recess for accommodating the resilient wedge when the retraction sleeve is in its proximal position. The interlock sleeve in its distal position may be arranged to support the resilient wedge from inside so as to prevent it from translating in distal direction. Thus, when the interlock sleeve is pressed against the injection site, the retraction sleeve is kept from retracting. Only after removal of the auto-injector from the injection site and consequent translation of the interlock sleeve into its proximal position the retraction sleeve may translate in distal direction and retract the needle into the housing.

A tubular syringe carrier may be arranged for holding the syringe and supporting it at its proximal end. Supporting the syringe at the proximal end is preferred over support at the finger flanges since the finger flanges are more frangible under load while the proximal or front end of the syringe is more robust. The syringe and the syringe carrier are arranged for joint axial translation. The syringe carrier is telescoped in the interlock sleeve, wherein at least one resilient second latch is arranged in the housing near the proximal end. In the as delivered state the resilient second latches extend inwards in a manner to prevent the syringe carrier from translating in proximal direction. The resilient second latches are arranged to be disengaged from the syringe carrier upon translation of the interlock sleeve in distal direction.

In a preferred embodiment at least one latch is provided for axially fixing the retraction sleeve in a maximum proximal position. The decoupling member is arranged to decouple the latch when being moved in proximal direction nearly into a maximum proximal position. When decoupled, the retraction sleeve is allowed to move in distal direction and retract the needle by means of the spring force which is no longer grounded at its distal end. Thus, retraction can only occur if the latches have been released and if the auto-injector has been removed from the injection site.

Preferably the plunger is arranged for pushing the syringe and/or the stopper in proximal direction. At least one (preferably two or more) resilient decoupling arm is arranged at the decoupling member. The decoupling arm exhibits an inner ramped surface bearing against a first shoulder of the plunger in proximal direction. The resilient decoupling arm is supportable by an inner wall of the retraction sleeve in order to prevent the decoupling arm from being flexed outward and slip past the first shoulder. In this state the plunger may be pushed in proximal direction by the decoupling member pushing against the first shoulder in order to insert the needle and inject the dose. At least one aperture is arranged in the retraction sleeve allowing the decoupling arm to be flexed outward by the first shoulder thus allowing the first shoulder to slip past the decoupling arm in proximal direction. This may happen when the injection is at least nearly finished. The decoupled plunger allows the syringe and needle to be refracted since it is no longer bearing against the decoupling member.

The syringe may be arranged for joint axial movement with a syringe holder which is slidably arranged in the retraction sleeve. The syringe holder is provided with at least one (preferably two or more) resilient syringe holder arm arranged distally, the syringe holder arm having an inclined surface for bearing against a second shoulder, which is arranged at the plunger proximally from the first shoulder. The syringe holder arm is supportable by an inner surface of the housing in order to prevent it from being flexed outward. Thus, when the trigger button is pressed the spring force forwarded by the plunger does not yet press against the stopper but against the syringe for forwarding it. Consequently, a so called wet injection is avoided, i.e. the liquid medicament is not leaking out of the hollow needle before the needle is inserted. A widened portion is provided in the housing for allowing the syringe holder arm to flex outwards when the syringe holder has nearly reached a maximum proximal position thus allowing the second shoulder to slip past the syringe holder arm and to switch load of the drive spring from the syringe to the stopper. This allows for defining the moment to start injecting the medicament.

A stud may be arranged at the distal end of the plunger. The retraction sleeve may have one (preferably two or more) resilient arm distally from the end face for holding the stud. The stud and/or the resilient arm have ramp features. Thus the resilient arm may be pushed outwards by the stud when the plunger is moved in proximal direction. The activating means comprise a trigger button arranged at the distal end of the auto-injector. The trigger button is axially moveable and has a rigid retainer for preventing each resilient arm from being flexed outward when the trigger button is in a maximum distal position. Upon pushing the trigger button in proximal direction the retainers are moved in proximal direction in a manner to allow the resilient arms to be flexed out by the stud biased by the drive spring in proximal direction. Thus the stud is allowed to slip past the resilient arms in proximal direction under load of the drive spring in order to start a needle insertion/injection/retraction cycle. The main advantages of this trigger mechanism are its simplicity, the low part count and a high reliability.

Usually the hollow needle is equipped with a protective needle shield for keeping the needle sterile and preventing it from being mechanically damaged. The protective needle shield is attached to the needle when the auto-injector or the syringe is assembled.

Preferably a cap is provided at the proximal end of the housing. A sheet metal clip is attached to the cap for joint axial movement and independent rotation. The sheet metal clip is arranged to extend through an orifice into the interlock sleeve when the cap is attached to the interlock sleeve. The sheet metal clip incorporates at least two barbs snapped into a circumferential notch or behind a shoulder of the protective needle shield. This allows for automatically engaging the sheet metal clip with the protective needle shield during assembly. When the cap is removed from the interlock sleeve in preparation of an injection the protective needle shield is reliably removed without exposing the user too high a risk to injure themselves.

The cap may be attachable to the housing by a screw connection. This allows for a low force removal of the protective needle shield.

The aperture in the retraction sleeve may extend at least almost to the position of the decoupling arms in the as delivered state up to their position at the end of dose. The aperture may be arranged to be angularly misaligned with respect to the decoupling arm when the retraction sleeve is in its proximal position so the plunger does not decouple from the decoupling member. The aperture and the retraction sleeve are also arranged to rotate so as to align the aperture with the decoupling arms upon translation of the retraction sleeve out of the proximal position in distal direction so the plunger and decoupling member decouple from each other thus allowing retraction of the plunger, stopper syringe and needle. This embodiment allows for starting the retraction at any point of the injection cycle.

The rotation into the aligned position may be achieved by a cam track arranged in the housing and a cam follower in the retraction sleeve. The cam track may be essentially parallel to a longitudinal axis of the auto-injector with a short angled section at its proximal end.

Alternatively the cam track may be arranged in the retraction sleeve and the cam follower in the housing.

The housing may have at least one viewing window for inspecting the syringe.

The auto-injector may preferably be used for subcutaneous or intra-muscular injection, particularly for delivering one of an analgetic, an anticoagulant, insulin, an insulin derivate, heparin, Lovenox, a vaccine, a growth hormone, a peptide hormone, a proteine, antibodies and complex carbohydrates.

The cap with the sheet metal spring may also be applied with other auto-injectors and injection devices.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given herein below and the accompanying drawings which are given by way of illustration only, and thus, are not limiting of the present invention, and wherein:

FIG. 7 is a longitudinal section of the auto-injector of FIG. 6, FIG. 8 is a cross section of the auto-injector of FIG. 7 in the section plane VIII-VIII, and FIG. 9 is an isometric detail view of a trigger button.

Corresponding parts are marked with the same reference symbols in all figures.

DETAILED DESCRIPTION

Figure 1A:
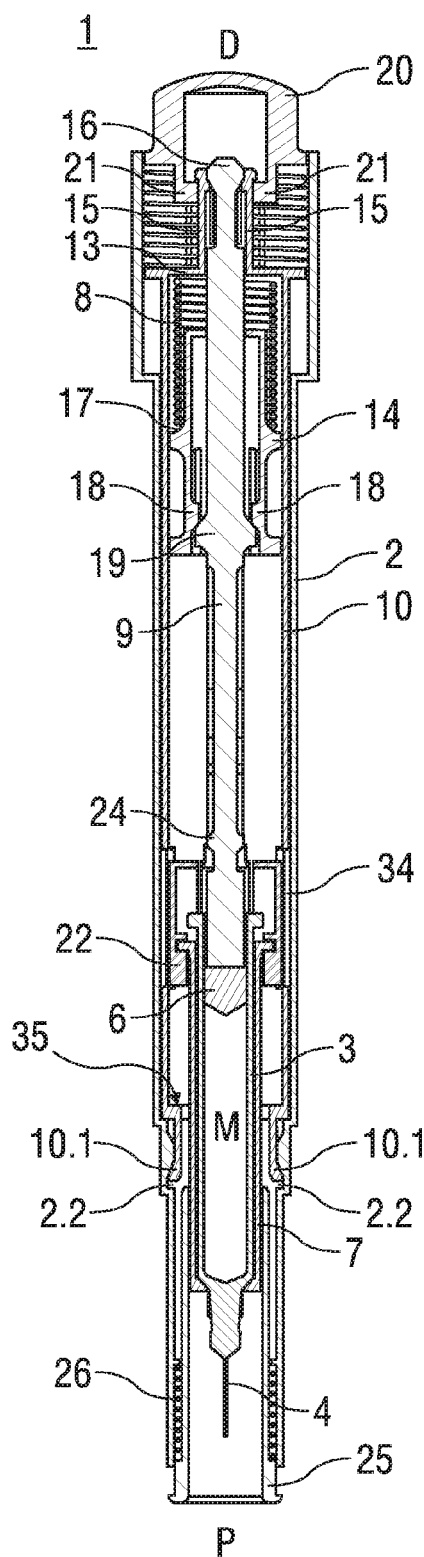
FIG. 1 are two longitudinal sections of an auto-injector with a single drive spring for advancing a syringe with a needle, injecting a dose of medicament and retracting the syringe and needle, the auto-injector as-delivered, FIG. 2 are two longitudinal sections of the auto-injector with a skin interlock sleeve pressed against an injection site, FIG. 3 are two longitudinal sections of another auto-injector with a modified trigger button.
Figure 1B:
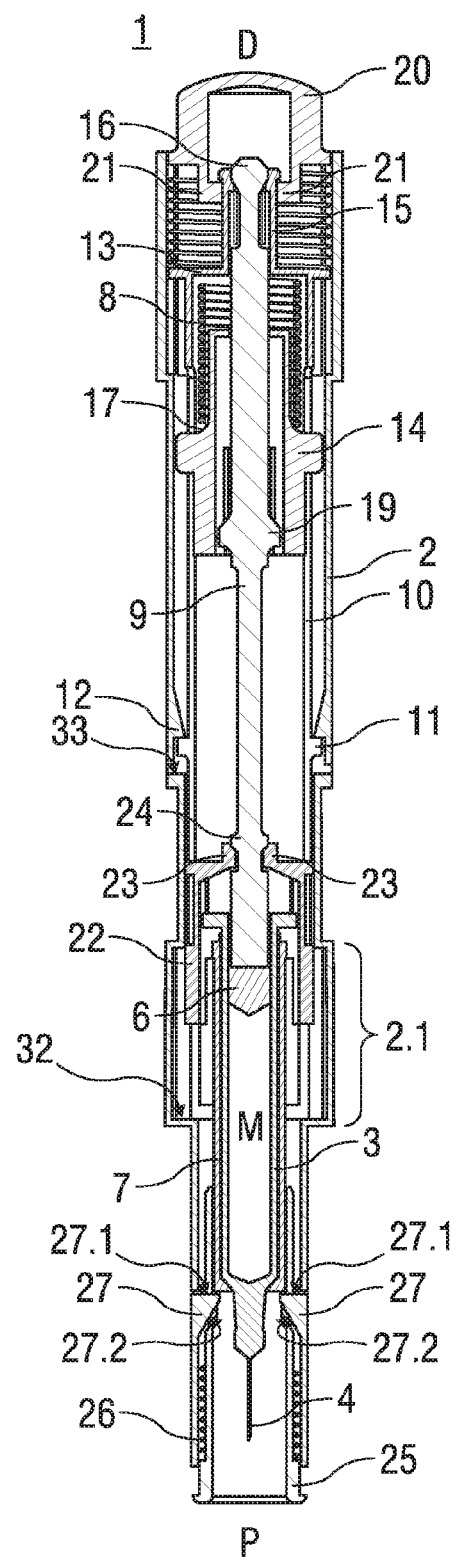

FIG. 1 shows two longitudinal sections in different section planes of an auto-injector 1, the different section planes approximately 90° rotated to each other. The auto-injector 1 comprises an elongate housing 2. A syringe 3, e.g. a Hypak syringe, with a hollow needle 4 is arranged in a proximal part of the auto-injector 1. When the auto-injector 1 or the syringe 3 is assembled a protective needle shield may be attached to the needle (not illustrated). A stopper 6 is arranged for sealing the syringe 3 distally and for displacing a liquid medicament M through the hollow needle 4. The syringe 3 is held in a tubular syringe carrier 7 and supported at its proximal end therein. A single drive spring 8 in the shape of a compression spring is arranged in a distal part of the auto-injector 1. A plunger 9 is arranged for forwarding the spring force of the drive spring 8.

Inside the housing 2 a retraction sleeve 10 is slidably arranged. Before the injection is triggered the retraction sleeve 10 is in a maximum proximal position and prevented from moving in distal direction D by means of stops 11 caught behind latches 12 in the housing 2. A distal end of the drive spring 8 bears against an end face 13 of the refraction sleeve 10. Due to the stops 11 and latches 12 the force of the drive spring 8 is thus reacted into the housing 2. The proximal end of the drive spring 8 bears against a decoupling member 14 arranged around the plunger 9. Distally from the end face 13 the retraction sleeve has two or more resilient arms 15 for holding a stud 16 and keeping it from being moved in proximal direction P. The stud 16 is arranged at the distal end of the plunger 9. The stud 16 and the resilient arms 15 have corresponding ramp features for pushing the resilient arms 15 apart in order to allow the stud 16 and the plunger 9 to move in proximal direction P.

The decoupling member 14 comprises a thrust face 17 for bearing against a proximal end of the drive spring 8. Proximally from the thrust face 17 two or more resilient decoupling arms 18 are provided at the decoupling member 14, the decoupling arms 18 having inner ramped surfaces bearing against a first shoulder 19 in the plunger 9 in proximal direction P. The resilient decoupling arms 18 are supported by an inner wall of the refraction sleeve 10 in this situation so they cannot flex outward and slip past the first shoulder 19.

A trigger button 20 is arranged at the distal end D of the auto-injector 1. The trigger button 20 may be pushed in proximal direction P in order to start an injection. As long as the trigger button 20 is not pushed the resilient arms 15 are caught between two or more retainers 21 arranged at the trigger button 20 so the resilient arms 15 cannot flex outward and the stud 16 although proximally biased by the drive spring 8 cannot slip through.

The syringe carrier 7 is engaged for joint axial movement with a syringe holder 22 which is slidably arranged in the retraction sleeve 10. The syringe holder 22 is provided with two or more resilient syringe holder arms 23 arranged distally. The syringe holder arms 23 have a respective inclined surface for bearing against a second shoulder 24 in the plunger 9 arranged proximally from the first shoulder 19. In the initial position shown in FIG. 1 the syringe holder arms 23 are supported by an inner surface of the housing 2 so they cannot flex outward and the second shoulder 24 cannot slip through. In order to support the syringe holder arms 23 at the housing 2 a respective number of apertures are provided in the retraction sleeve 10.

Two resilient wedges 10.1 are arranged at a proximal end of the retraction sleeve 10. The housing 2 has two recesses 2.2 arranged to accommodate the resilient wedges 10.1 when the retraction sleeve 10 is in its proximal position.

A skin interlock sleeve 25 is telescoped in the proximal end P of the housing 2. The syringe carrier 7 in turn is telescoped in the interlock sleeve 25. The interlock sleeve 25 is biased in proximal direction P by an interlock spring 26. Two resilient second latches 27 are arranged in the housing 2 near the proximal end P. In the state as delivered the second latches 27 are relaxed and extend inwardly through respective apertures 25.1 in the interlock sleeve 25 in a manner to prevent the syringe carrier 7 from translating in proximal direction P by the syringe carrier 7 abutting against respective distal faces 27.1 of the second latches 27. The syringe carrier 7, the syringe 3 and the needle 4 can therefore not be forwarded when pushed by the plunger 9.

In order to start an injection the auto-injector 1 has to be pressed against the injection site, e.g. a patient's skin. As a result the interlock sleeve 25 translates in distal direction D into the housing 2 (see FIG. 2). A proximal edge of the aperture 25.1 pushes against a proximal ramp 27.2 of the second latch 27 thereby flexing the second latch 27 outwards so the syringe carrier 7 comes clear of the distal faces 27.1 and may now translate in proximal direction P. When translated into the housing 2 as in FIG. 2 a distal end of the interlock sleeve 25 supports the resilient wedges 10.1 from inside so they cannot be flexed inwards thus preventing the retraction sleeve 10 from translating in distal direction D.

The trigger button 20 can now be pushed to release the drive spring 8 in order to insert the needle 4 into the injection site and to inject the medicament M.

If the auto-injector 1 is removed from the injection site without operating the trigger button 20 the interlock sleeve 25 will translate back into its proximal position under load of the interlock spring 26. The second latches 27 will flex inwards and block the syringe carrier 7 so the auto-injector 1 is in its as delivered state again.

The sequence of operation can be reversed in this embodiment, i.e. the trigger button 20 may be pushed before pressing the auto-injector 1 against the injection site.

When the trigger button 20 is pushed the retainers 21 are pushed in proximal direction P so the resilient arms 15 are allowed to flex outward. Under load of the drive spring 8 the inclined surfaces of the stud 16 force the resilient arms 15 apart until the stud 16 can slip through.

The second shoulder 24 pushes the syringe holder 22, syringe carrier 7 and syringe 3 forward while no load is exerted onto the stopper 6. The hollow needle 4 appears from the proximal end P and is inserted into an injection site, e.g. a patient's skin.

The forward movement continues until the syringe holder 22 bottoms out at a first abutment 32 in the housing 2. The travel from the initial position up to this point defines an injection depth, i.e. needle insertion depth.

When the syringe holder 22 has nearly bottomed out the resilient syringe holder arms 23 have reached a widened portion 2.1 of the housing 2 where they are no longer supported by the inner wall of the housing 2. However, since the force required to insert the needle 4 is relatively low the second shoulder 24 will continue to drive forward the syringe holder 22 until proximal travel is halted at the first abutment 32. At this point the syringe holder arms 23 are flexed out by the continued force of the second shoulder 24 and allow it to slip through. Now the plunger 9 no longer pushes against the syringe holder 22 but against the stopper 6 for expelling the medicament M from the syringe 3 and injecting it into or through the patient's skin.

When the stopper 6 has nearly bottomed out in the syringe 3 the decoupling member 14 has reached a position where it pushes against the latches 12 in a manner to decouple the refraction sleeve 10 from the housing 2. Thus the drive spring 8 is no longer grounded with its distal end in the housing 2 by the latches 12. Instead, as soon as the decoupling member 14 has bottomed out at a second abutment 33 the proximal end of the drive spring 8 gets grounded in the housing 2 while its distal end is pulling the refraction sleeve 10 in distal direction D.

Just before the decoupling member 14 decouples the retraction sleeve 10 from the housing 2 the decoupling arms 18 reach an aperture 34 in the retraction sleeve 10 so they are no longer kept from being flexed outward. The decoupling arms 18 are thus pushed outward by the first shoulder 19 pushing against its ramped surfaces so the first shoulder 19 can slip through in distal direction D as soon as the decoupling member 14 has hit the second abutment 33.

Although the latches 12 are disengaged now, the retraction sleeve 10 may not yet slide in distal direction D because of the resilient wedges 10.1 being held in the recess 2.2 between the housing 2 and the interlock sleeve 25 as long as the interlock sleeve 25 is in its distal position by the auto-injector 1 being kept pushed against the injection site.

If the auto-injector 1 is taken away from the injection site the interlock sleeve 25 will return to its proximal position (as in FIG. 1) under load of the interlock spring 26 so the resilient wedges 10.1 are no longer supported from inside. Since the drive spring 8 tries to pull the retraction sleeve 10 in distal direction D, distal ramps of the resilient wedges 10.1 move along proximal ramps of the recesses 2.2 thereby flexing the resilient wedges inwards as the retraction sleeve 10 starts translating in distal direction.

The syringe holder 22 is taken along in distal direction D by the retraction sleeve 10, e.g. by a front face 35. Thus the syringe 3 and needle 4 are retracted into a safe position inside the housing 2, e.g. into the initial position. The plunger 9, no longer bearing against the decoupling arms 18 is pulled back too.

Figure 2A:
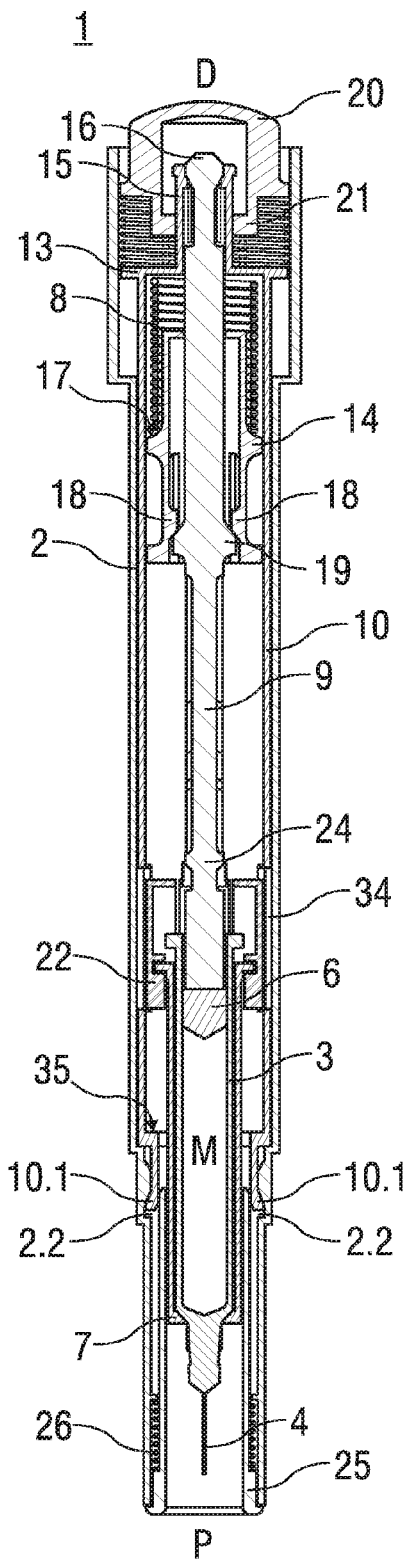
Figure 2B:
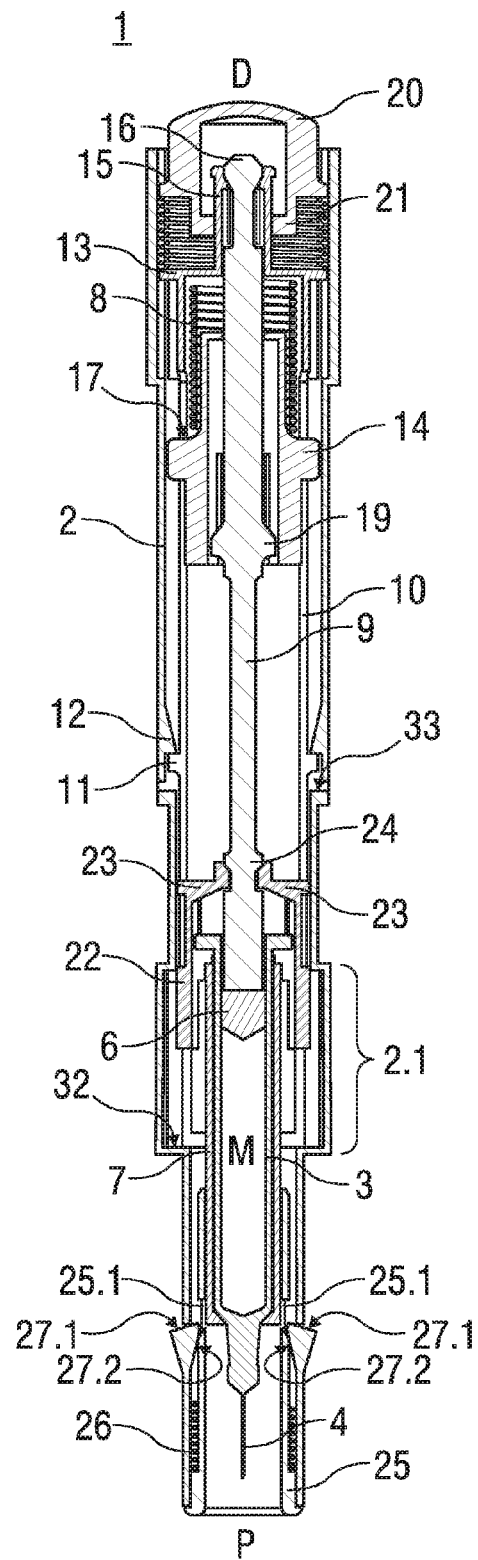

In the embodiment illustrated in FIGS. 1 and 2 the latches 12 and the stops 11 at the retraction sleeve 10 are not absolutely required. Retraction can be triggered by removal of the auto-injector 1 from the injection site alone. However, the latches 12 and the stops 11 facilitate assembly of the auto-injector 1 and give an initial position to the retraction sleeve 10. Furthermore, the stops 11 as well as lugs on the decoupling member 14 for disengaging the latches 12 and the stops 11 run in a slot 2.6 in the housing 2 thus preventing the retraction sleeve 10 and the decoupling member 14 from rotating.

Figure 3A:
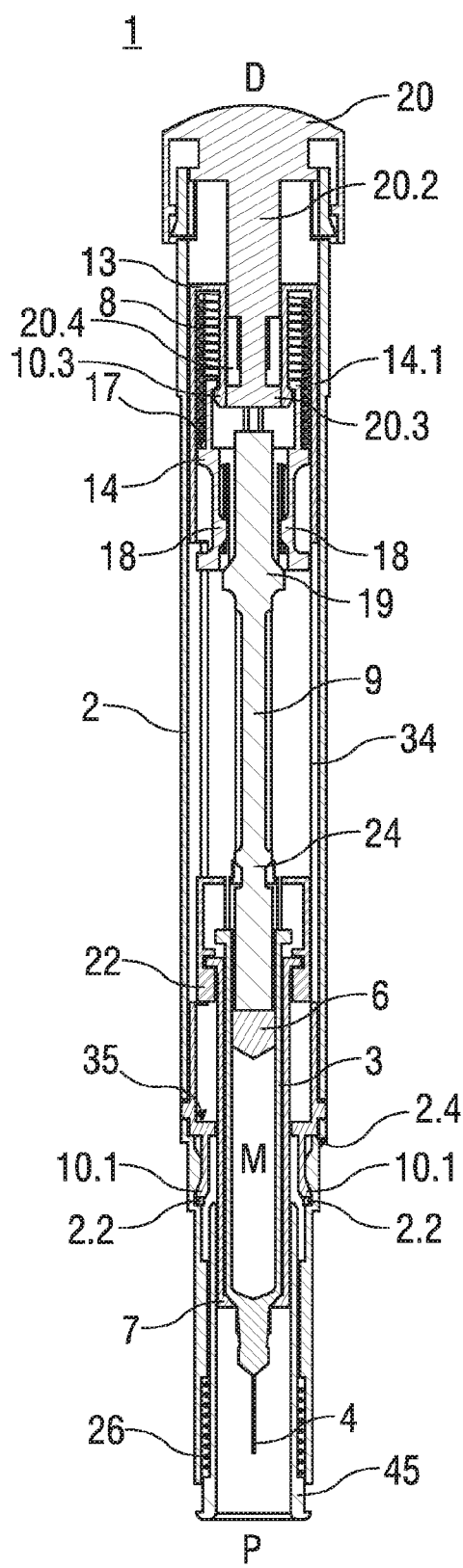
Figure 3B:
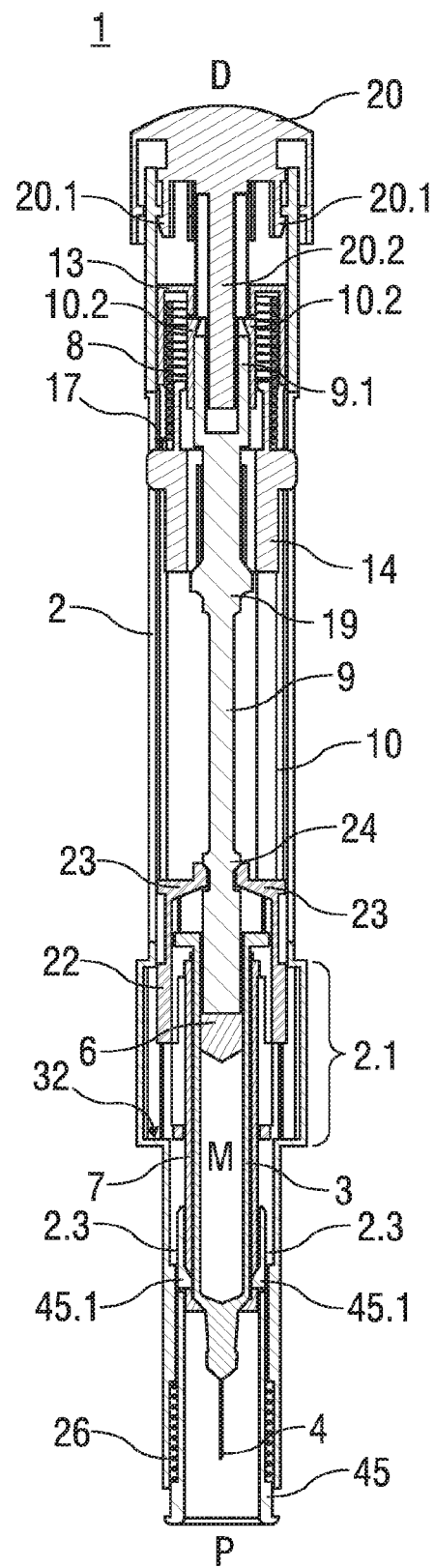

FIG. 3 shows two longitudinal sections in different section planes of another embodiment of an auto-injector 1, the different section planes approximately 90° rotated to each other. The auto-injector 1 comprises an elongate housing 2. A syringe 3, e.g. a Hypak syringe, with a hollow needle 4 is arranged in a proximal part of the auto-injector 1. When the auto-injector 1 or the syringe 3 is assembled a protective needle shield may be attached to the needle (not illustrated). A stopper 6 is arranged for sealing the syringe 3 distally and for displacing a liquid medicament M through the hollow needle 4. The syringe 3 is held in a tubular syringe carrier 7 and supported at its proximal end therein. A single drive spring 8 in the shape of a compression spring is arranged in a distal part of the auto-injector 1. A plunger 9 is arranged for forwarding the spring force of the drive spring 8.

Inside the housing 2 a retraction sleeve 10 is slidably arranged. Before the injection is triggered the retraction sleeve 10 is in a maximum proximal position abutting against a stop 2.4 in the housing 2. A distal end of the drive spring 8 bears against an end face 13 of the retraction sleeve 10. The proximal end of the drive spring 8 bears against a decoupling member 14 arranged around the plunger 9.

The decoupling member 14 comprises a thrust face 17 for bearing against a proximal end of the drive spring 8. Proximally from the thrust face 17 two or more resilient decoupling arms 18 are provided at the decoupling member 14, the decoupling arms 18 having inner ramped surfaces arranged for bearing against a first shoulder 19 in the plunger 9 in proximal direction P. In the as delivered state in FIG. 3 the first shoulder 19 is situated a small distance proximally from the ramped surfaces of the decoupling arms 18. The resilient decoupling arms 18 may be supported by an inner wall of the retraction sleeve 10 for preventing them from being flexed outward and slip past the first shoulder 19. Apertures 34 are provided in the retraction sleeve 10 for allowing the decoupling arms 18 to flex outwards.

A trigger button 20 is arranged at the distal end D of the auto-injector 1. The trigger button 20 is arranged to be pushed in proximal direction P in order to start an injection.

The syringe carrier 7 is engaged for joint axial movement with a syringe holder 22 which is slidably arranged in the retraction sleeve 10. The syringe holder 22 is provided with two or more resilient syringe holder arms 23 arranged distally. The syringe holder arms 23 have a respective inclined surface for bearing against a second shoulder 24 in the plunger 9 arranged proximally from the first shoulder 19. In the initial position shown in FIG. 3 the syringe holder arms 23 are supported by an inner surface of the housing 2 so they cannot flex outward and the second shoulder 24 cannot slip through. In order to support the syringe holder arms 23 at the housing 2 a respective number of apertures are provided in the retraction sleeve 10.

Two resilient wedges 10.1 are arranged at a proximal end of the retraction sleeve 10. The housing 2 has two recesses 2.2 arranged to accommodate the resilient wedges 10.1 when the retraction sleeve 10 is in its proximal position.

A skin interlock sleeve 45 is telescoped in the proximal end P of the housing 2. The syringe carrier 7 in turn is telescoped in the interlock sleeve 45. The interlock sleeve 45 is biased in proximal direction P by an interlock spring 26.

In the as delivered state as shown in FIG. 3 the interlock sleeve 45 is coupled with the syringe carrier 7 by resilient clips 45.1 provided in the interlock sleeve 45. The clips 45.1 are engaged in a respective recess in the syringe carrier 7 and outwardly supported by the housing 2 so they cannot flex outward. Hence, in the state as delivered, the interlock sleeve 45, the syringe carrier 7 with the syringe 3 and the needle 4, the syringe holder 22 and the plunger 9 are coupled for joined axial translation. The recess in the syringe carrier 7 and the clip 45.1 have ramps arranged to flex the clip 45.1 outwards when the syringe carrier 7 and the interlock sleeve 45 are pushed against each other in longitudinal direction.

The syringe carrier 7, the syringe 3 and the needle 4 can therefore not be forwarded when pushed by the plunger 9.

Figure 4:
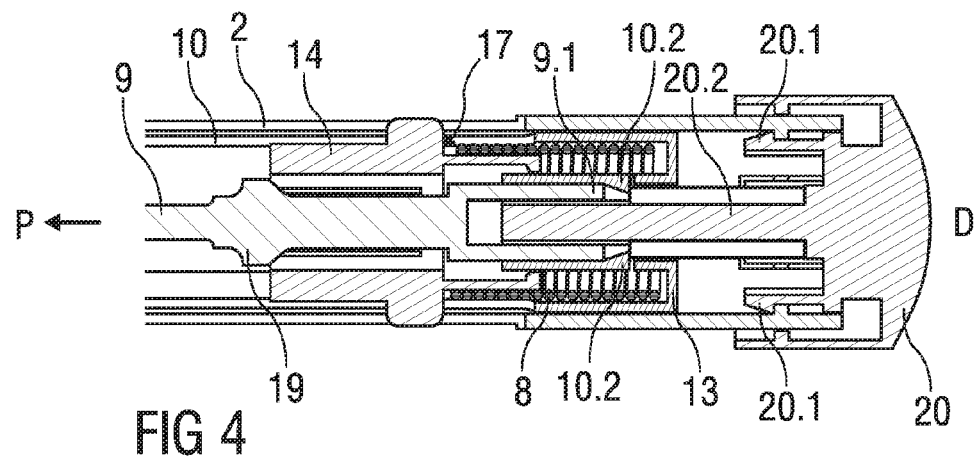
FIG. 4 is a detail view of the trigger button of FIG. 3 prior to actuation, FIG. 5 are two detail views of the trigger button of FIG. 3 upon actuation, FIG. 6 are two isometric views of an embodiment of the auto-injector with the capability to immediately retract the syringe upon removal of the auto-injector from the injection site.
Figure 5A:
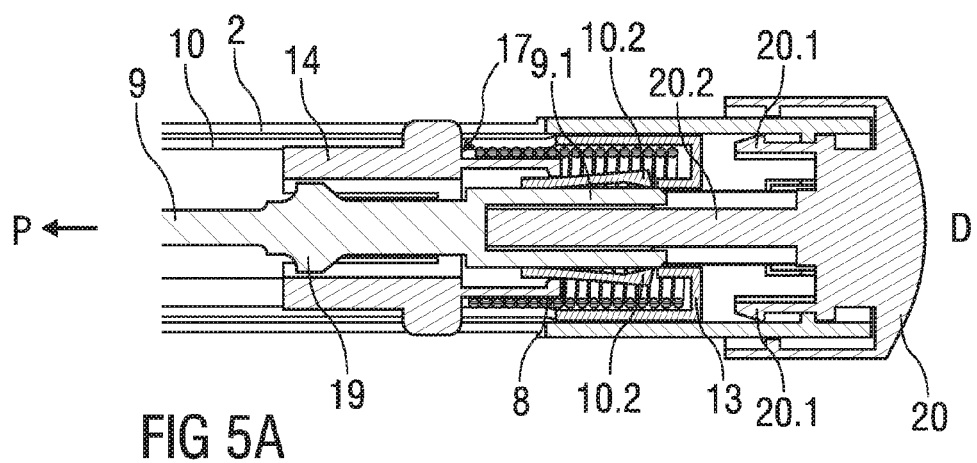
Figure 5B:
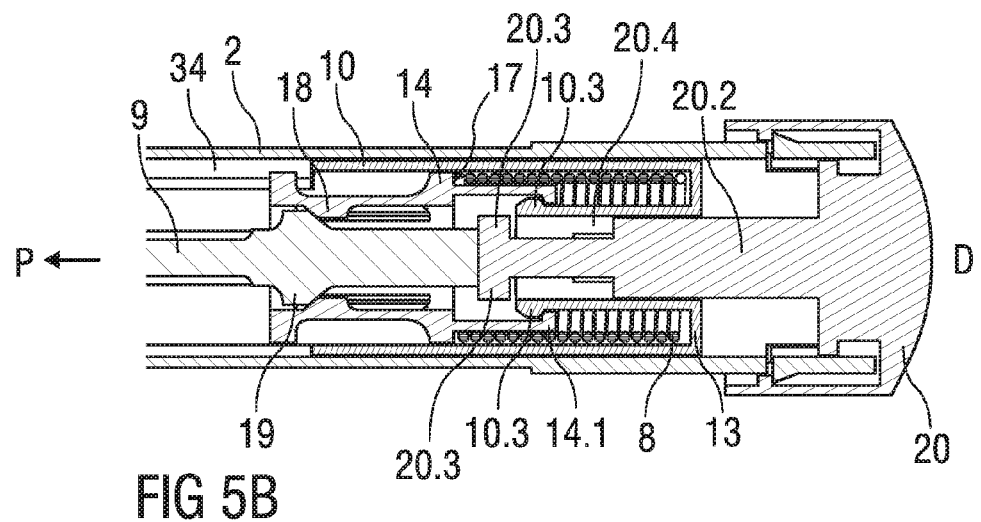

The trigger button 20 is secured on the housing 2 by means of clips 20.1 so it cannot translate in distal direction D further than shown in FIG. 4. A central shaft 20.2 extends from the trigger button 20 in proximal direction towards the plunger 9. Another set of resilient clips 10.2 are arranged on the retraction sleeve 10 proximally from the end face 13 inside the drive spring 8 arranged for abutting against a shoulder 20.5 in the central shaft 20.2 in a manner to prevent the trigger button 20 from being actuated in the as delivered state (see FIG. 9). The retraction sleeve 10 can not translate in proximal direction P due to its proximal end abutting against the stop 2.4. The resilient clips 10.2 may be disengaged from the trigger button 20 by respective bars 9.1 extending distally from the distal end of the plunger 9 upon translation of the plunger 9 in distal direction D. A set of resilient catches 10.3 (shown in FIG. 5B) are arranged on the retraction sleeve 10 proximally from the end face 13 inside the drive spring 8 for engaging respective catches 14.1 extending distally from the decoupling member 14. The catches 14.1 and 10.3 are engaged with each other in a manner to prevent the decoupling member 14 from translating in proximal direction P as long as the trigger button 20 is not pushed. This occurs by respective dogs 20.3 on the proximal end of the trigger button 20 inwardly supporting the catches 10.3 so they cannot flex inwards. The catches 14.1 are outwardly supported by the drive spring 8 so they cannot flex outwards. When the trigger button 20 is actuated the dogs 20.3 are translated in proximal direction P so the catches 10.3 may flex inwards into spaces 20.4 as ramped surfaces of the catches 10.3 and 14.1 slide along each other under load of the drive spring 8.

In order to start an injection the auto-injector 1 has to be pressed against the injection site, e.g. a patient's skin. As a result the interlock sleeve 45 translates in distal direction D into the housing 2 by a small distance taking with it the syringe carrier 7, the syringe 3 with the needle 4, the syringe holder 22 and the plunger 9 until the first shoulder 19 meets the ramped surfaces of the decoupling arms 18. At the same time the clips 45.1 enter a space 2.3 in the housing 2 where they are no longer supported outwardly so they may now flex outwards for decoupling the interlock sleeve 45 from the syringe carrier 7.

When translated into the housing 2 a distal end of the interlock sleeve 45 supports the resilient wedges 10.1 from inside so they cannot be flexed inwards thus preventing the retraction sleeve 10 from translating in distal direction D.

As the plunger 9 translates in distal direction D the bars 9.1 disengage the clips 10.2 so the trigger button 20 becomes unlocked and may now be actuated.

If the auto-injector 1 is removed from the injection site without operating the trigger button 20 the interlock sleeve 45 will translate back into its proximal position under load of the interlock spring 26.

As the trigger button 20 is pushed dogs 20.3 no longer support catches 10.3 and so the catches 10.3 are flexed inwards into the spaces 20.4 as the ramped surfaces of the catches 10.3 and 14.1 slide along each other under load of the drive spring 8. The drive spring 8 now advances the decoupling member 14 and thus the plunger 9 in proximal direction.

The second shoulder 24 pushes the syringe holder 22, syringe carrier 7 and syringe 3 forward while no load is exerted onto the stopper 6. The hollow needle 4 appears from the proximal end P and is inserted into the injection site, e.g. a patient's skin.

The forward movement continues until the syringe holder 22 bottoms out at a first abutment 32 in the housing 2. The travel from the initial position up to this point defines an injection depth, i.e. needle insertion depth.

When the syringe holder 22 has nearly bottomed out the resilient syringe holder arms 23 have reached a widened portion 2.1 of the housing 2 where they are no longer supported by the inner wall of the housing 2. However, since the force required to insert the needle 4 is relatively low the second shoulder 24 will continue to drive forward the syringe holder 22 until proximal travel is halted at the first abutment 32. At this point the syringe holder arms 23 are flexed out by the continued force of the second shoulder 24 and allow it to slip through. Now the plunger 9 no longer pushes against the syringe holder 22 but against the stopper 6 for expelling the medicament M from the syringe 3 and injecting it into or through the patient's skin.

When the stopper 6 has bottomed out in the syringe 3, the retraction sleeve 10 may not yet slide in distal direction D because of the resilient wedges 10.1 being held in the recess 2.2 between the housing 2 and the interlock sleeve 45 as long as the interlock sleeve 45 is in its distal position by the auto-injector 1 being kept pushed against the injection site.

If the auto-injector 1 is taken away from the injection site the interlock sleeve 45 will return to its proximal position (as in FIG. 3) under load of the interlock spring 26 so the resilient wedges 10.1 are no longer supported from inside. Since the drive spring 8 tries to pull the retraction sleeve 10 in distal direction D, distal ramps of the resilient wedges 10.1 move along proximal ramps of the recesses 2.2 thereby flexing the resilient wedges 10.1 inwards as the retraction sleeve 10 starts translating in distal direction D.

The syringe holder 22 is taken along in distal direction D by the retraction sleeve 10, e.g. by a front face 35. Thus the syringe 3 and needle 4 are retracted into a safe position inside the housing 2, e.g. into the initial position. The plunger 9, no longer bearing against the decoupling arms 18 is pulled back too.

The auto-injector 1 of FIG. 3 is arranged to retract the syringe 3 and needle 4 at any time during the injection if pulled away from the skin. In FIGS. 1 and 2 the retraction sleeve held by the interlock sleeve 25 if released before the end of injection will not retract the syringe 3 if the decoupling member 14 does not release the plunger 9 at the same time. The plunger 9 is only released at its end of travel when the decoupling member 14 meets the aperture 34.

Figure 6A:
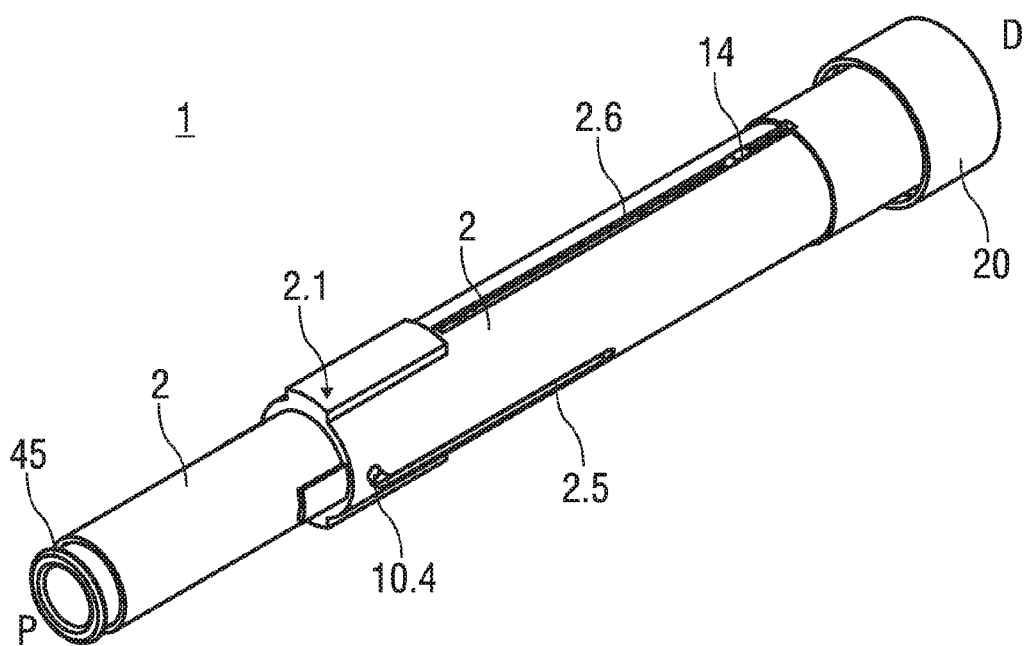
Figure 6B:
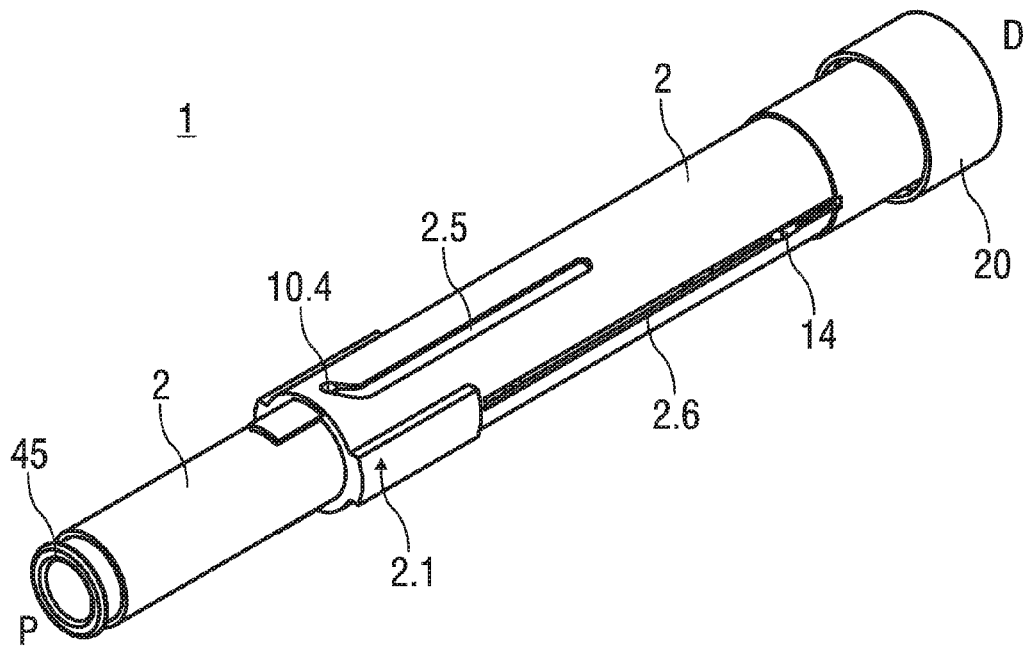

In order to retract the syringe 3 before the end of injection the aperture 34 needs to be available at any time during plunger travel. The aperture 34 therefore extends right to the position of the decoupling arms 18 in the as delivered state. However, the aperture is angularly misaligned with respect to the decoupling arms 18 by a small angle so the decoupling member 14 and the plunger 9 cannot decouple. When the auto-injector 1 is removed from the injection site, the interlock sleeve 45 translates in proximal direction under load of the interlock spring 26 so the resilient wedges 10.1 are no longer supported from inside. Since the drive spring 8 tries to pull the retraction sleeve 10 in distal direction D, distal ramps of the resilient wedges 10.1 move along proximal ramps of the recesses 2.2 thereby flexing the resilient wedges inwards as the retraction sleeve 10 starts translating in distal direction. The refraction sleeve 10 is arranged to rotate in this situation by a small angle thus aligning the aperture 34 and the decoupling arms 18, so the decoupling member 18 decouples from the plunger 9 and the syringe 3 and the needle 4 are retracted into a safe position inside the housing 2. Decoupling member 14 and hence decoupling arms 18 are prevented from rotating in housing 2 by one or more lugs on decoupling member 14 which engage in longitudinal slots 2.6 in housing 2, as shown in FIGS. 6a and 6b. In order to make the retraction sleeve 10 rotate a cam track 2.5 is arranged in the housing 2 and a cam follower 10.4 in the retraction sleeve 10 (see FIGS. 6a and 6b). The cam track 2.5 is essentially parallel to the longitudinal axis of the auto-injector 1 with a short angled section at its proximal end. As long as the cam follower 10.4 runs in the parallel section of the cam track, the retraction sleeve 10 is prevented from rotating.

FIG. 7 shows the auto-injector of FIG. 3 with the actuated trigger button 20. FIG. 8 is a cross section in the section plane VIII-VIII illustrating the angular misalignment before the retraction is triggered.

In an alternative embodiment the auto-injector 1 of FIG. 3 may have the aperture 34 in the retraction sleeve 10 as in FIGS. 1 and 2. In this case the needle retraction would occur only at the end of dose.

Likewise, the auto-injector 1 of FIGS. 1 and 2 could be combined with the aperture 34, the cam track 2.5 and the cam follower 10.4 of FIGS. 3 to 8 in order to provide immediate needle retraction at any point during the injection cycle.

The cam track may likewise be arranged in the retraction sleeve 10 and the cam follower in the housing 2.

The housing 2 may have at least one viewing window for inspecting the syringe 3.

The auto-injector 1 may preferably be used for subcutaneous or intra-muscular injection, particularly for delivering one of an analgetic, an anticoagulant, insulin, an insulin derivate, heparin, Lovenox, a vaccine, a growth hormone, a peptide hormone, a proteine, antibodies and complex carbohydrates.

The aforementioned arrangement for coupling the plunger 9 to either, the syringe 3 or the stopper 6, may be applied in any auto-injector having a plunger for forwarding a force of a drive means to a syringe with a stopper. The primary advantage of this arrangement ensures the load from the drive means is not transferred directly to the stopper until the needle is inserted in the patient, thus avoiding a wet injection. The arrangement comprises the syringe holder 22 and associated syringe holder arms 23, a shoulder (e.g. the second shoulder 24) on the plunger 9, the support of the holder arms 23 by an inner surface in order to prevent them from flexing out in a first position and, a widened portion 2.1 for allowing them to flex radially and to disconnect from the plunger when in a more proximal position. The spring means or other drive means, the ability to retract the syringe or to forward a needle shroud after injection and other features described herein are not required for the prevention of a wet injection.

The invention claimed is:

1. An auto-injector for administering a dose of a liquid medicament, comprising:
   an elongate housing;
   a syringe in the elongate housing, the syringe comprising a hollow needle and a stopper for sealing the syringe and displacing the medicament, the housing having a distal end and a proximal end with an orifice intended to be applied against an injection site, wherein the syringe is slidably arranged with respect to the housing;
   a spring capable of, upon activation:
   pushing the syringe from a retracted position inside the housing into an advanced position through the orifice and past the proximal end,
   operating the syringe to supply the dose of medicament, and
   retracting the syringe with the needle into the retracted position after delivering the medicament;
   a trigger arranged to lock the spring in a pressurized state prior to manual operation and capable of, upon manual operation, releasing the spring for injection, wherein the spring comprises a single drive spring in the shape of a compression spring, the drive spring having a proximal end, a distal end, and a ground, and the drive spring being arranged to have its ground in the housing at the distal end of the drive spring for advancing the needle and for injecting the dose of medicament via a plunger and arranged to have its ground in the housing switched to the proximal end of the drive spring for retracting the syringe;
   an interlock sleeve that is telescoped in the proximal end of the housing, the interlock sleeve translatable in a longitudinal direction between a proximal position and a distal position and biased in a proximal direction in a manner to protrude from the housing in the proximal position, wherein in its proximal position the interlock sleeve is arranged to be coupled to the syringe in the syringe's retracted position, and wherein the interlock sleeve in its distal position is arranged to be decoupled from the syringe; and
   a syringe carrier holding the syringe and supporting a proximal end of the syringe, the syringe carrier being configured to be telescoped in the interlock sleeve, and the syringe and the syringe carrier being arranged for joint axial translation.

2. The auto-injector according to claim 1, wherein the interlock sleeve in its distal position is arranged to inhibit release of the ground at the distal end of the drive spring.

3. The auto-injector according to claim 1, further comprising a retraction sleeve axially movably arranged in the housing,
   wherein the drive spring is arranged inside the retraction sleeve with the distal end of the drive spring bearing against a distal end face and with the proximal end of the drive spring bearing against a thrust face of a decoupling member,
   wherein a resilient wedge is arranged at the proximal end of the retraction sleeve,
   wherein the housing has a recess for accommodating the resilient wedge when the retraction sleeve is in its proximal position, and
   wherein the interlock sleeve in its distal position is arranged to support the resilient wedge from inside to inhibit the resilient wedge from translating in a distal direction.

4. The auto-injector according to claim 3, further comprising a latch for axially fixing the retraction sleeve in a maximum proximal position,
   wherein the decoupling member is movable in the proximal direction nearly into a maximum proximal position to decouple the latch, thus allowing the retraction sleeve to move in the distal direction to retract the needle.

5. The auto-injector according to claim 3, further comprising:
   at least two resilient decoupling arms arranged at the decoupling member, the decoupling arms having inner ramped surfaces bearing against a first shoulder of the plunger in the proximal direction, wherein the resilient decoupling arms are supportable by an inner wall of the retraction sleeve to inhibit the decoupling arms from being flexed outward and slipping past the first shoulder; and
   at least one aperture arranged in the retraction sleeve to receive the decoupling arms when the first shoulder causes the decoupling arms to move outward, thus allowing the first shoulder to slip through the decoupling arms in the proximal direction, wherein the plunger is arranged for pushing the syringe and/or the stopper in the proximal direction.

6. The auto-injector according to claim 5, wherein the aperture extends at least almost to the position of the decoupling arms in an as delivered state,
   wherein the aperture is arranged to be angularly misaligned with respect to the decoupling arms when the retraction sleeve is in its proximal position, and wherein the aperture is arranged to rotate so as to align with the decoupling arms upon translation of the retraction sleeve out of the proximal position in the distal direction.

7. The auto-injector according to claim 6, further comprising:
a cam track arranged in the housing; and
a cam follower arranged in the retraction sleeve,
wherein the cam track is essentially parallel to a longitudinal axis of the auto-injector with a short angled section at its proximal end.

8. The auto-injector according to claim 6, further comprising:
a cam track arranged in the retraction sleeve; and
a cam follower arranged in the housing,
wherein the cam track is essentially parallel to a longitudinal axis of the auto-injector with a short angled section at its proximal end.

9. The auto-injector according to claim 3, wherein the syringe is arranged for joint axial movement with a syringe holder slidably arranged in the retraction sleeve,
wherein the syringe holder is provided with at least two resilient syringe holder arms arranged distally, the syringe holder arms having a respective inclined surface for bearing against a second shoulder of the plunger arranged proximally from a first shoulder of the plunger,
wherein the syringe holder arms are supportable by an inner surface of the housing to inhibit the syringe holder arms from being flexed outward, and
wherein a widened portion is provided in the housing for allowing the syringe holder arms to flex outwards when the syringe holder has nearly reached a maximum proximal position thus allowing the second shoulder to slip through the syringe holder arms and to switch load of the drive spring from the syringe to the stopper.

10. The auto-injector according to claim 3, further comprising a stud arranged at a distal end of the plunger,
wherein the retraction sleeve has two or more resilient arms positioned distally from the distal end face for holding the stud, the stud and/or the resilient arms having ramp features such that the resilient arms are pushed apart by the stud when the plunger is moved in the proximal direction,
wherein the trigger comprises a trigger button arranged at a distal end of the auto-injector, the trigger button axially moveable and having at least two rigid retainers to inhibit the resilient arms from being flexed outward when the trigger button is in a distal position, and
wherein, upon pushing the trigger button in the proximal direction the retainers are moved in the proximal direction in a manner to allow the resilient arms to be flexed out by the stud biased by the drive spring in the proximal direction thus allowing the stud to slip past the resilient arms in the proximal direction.

11. The auto-injector according to claim 1, further comprising a resilient latch arranged in the housing near the proximal end,
wherein in an as delivered state the resilient latch extends inwards to inhibit the syringe carrier from translating in the proximal direction, and
wherein the resilient latch is arranged to be disengaged from the syringe carrier upon translation of the interlock sleeve in a distal direction.

12. The auto-injector according to claim 1, wherein the interlock sleeve, the housing, and the syringe carrier are translatable relative to one another.

13. The auto-injector according to claim 1, wherein the interlock sleeve is configured to be pressed against the injection site of a patient such that the interlock sleeve translates in a distal direction into the housing.

14. The auto-injector according to claim 1, wherein the interlock sleeve is arranged to push a latch outward such that the latch disengages from the syringe carrier when the interlock sleeve is in the distal position.

15. The auto-injector according to claim 1, wherein the syringe carrier is tubular.

16. The auto-injector according to claim 1, wherein the interlock sleeve is arranged to inhibit the drive spring from pushing the syringe from the retracted position into the advanced position when the interlock sleeve is in the proximal position.

* * * * *